(12) United States Patent
Pierre et al.

(10) Patent No.: US 8,048,137 B2
(45) Date of Patent: Nov. 1, 2011

(54) TUBE BLANKET

(75) Inventors: Joseph Pierre, Brockton, MA (US); Rachel Starr, Randolph, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1305 days.

(21) Appl. No.: 11/646,458

(22) Filed: Dec. 28, 2006

(65) Prior Publication Data
US 2008/0161891 A1 Jul. 3, 2008

(51) Int. Cl.
*A61F 7/00* (2006.01)

(52) U.S. Cl. .................. 607/107; 607/104; 607/109

(58) Field of Classification Search .................. 607/107, 607/109
See application file for complete search history.

(56) References Cited

U.S. PATENT DOCUMENTS

| 4,867,230 | A |   | 9/1989  | Voss             |         |
|-----------|---|---|---------|------------------|---------|
| 5,165,400 | A | * | 11/1992 | Berke            | 607/104 |
| 5,300,101 | A |   | 4/1994  | Augustine et al. |         |
| 5,674,269 | A |   | 10/1997 | Augustine        |         |
| 5,675,848 | A |   | 10/1997 | Kappel           |         |
| 6,176,870 | B1|   | 1/2001  | Augustine        |         |
| 6,241,756 | B1|   | 6/2001  | Kappel           |         |
| 6,277,144 | B1|   | 8/2001  | Tomic-Edgar et al.|        |
| 6,493,889 | B2| * | 12/2002 | Kocurek          | 5/423   |
| 6,689,155 | B2|   | 2/2004  | Gammons et al.   |         |
| 6,699,270 | B2|   | 3/2004  | Gammons et al.   |         |
| 6,827,729 | B2|   | 12/2004 | Gammons et al.   |         |
| 2002/0100121 | A1 | | 8/2002 | Kocurek          |         |
| 2003/0023290 | A1 | | 1/2003 | Gammons          |         |
| 2005/0125048 | A1 | | 6/2005 | Paolini          |         |

FOREIGN PATENT DOCUMENTS
WO     03/011110     2/2003
* cited by examiner

*Primary Examiner* — Roy Gibson
(74) *Attorney, Agent, or Firm* — Louis Woo

(57) ABSTRACT

Each leg of a U tube blanket is configured to have at least one row of holes extending substantially along the length thereof. The size of the holes is incrementally increased from the proximal portion that is closest to the air inlet cross section of the blanket where heated air is input to the blanket for inflating the same to the distal portion of the legs of the blanket. For an embodiment of the inventive blanket, the plurality of vent holes along each leg of the blanket are grouped into a number of sections, for illustration purposes three, with the vent holes in each section having the same dimension. With the size of the holes being incrementally larger along the leg away from the heat source, a greater amount of warm air is output at the distal portion of the blanket to compensate for the distance the warm air needs to travel before it is vented from the blanket. As a result, a substantially evenly distributed bath of warm air is output from the legs of the blanket to the sides of the patient so that the patient is evenly warmed along his entire body. Straps that are separable from the legs of the blanket are provided to secure the blanket to the patient.

10 Claims, 1 Drawing Sheet

TUBE BLANKET

FIELD OF THE INVENTION

The present invention relates to convective warming blankets and more specifically to a U-shaped tube blanket that is adapted to be placed around a patient.

BACKGROUND OF THE INVENTION

Prior to the instant invention, tube blankets, which may be in the shape of U tubes, are formed with vent holes that have the same dimension. Accordingly, the warm air that outputs from the portions of the U tube blanket that are remote from the air input source tends to be colder than the warm air that outputs from the portions of the blanket close to where the heated air from a convective warmer is input. Thus, uneven warming of the patient results.

There is therefore a need for a U-shaped type convective warming blanket that can bathe a patient with an evenly distributed envelope of warm air.

SUMMARY OF THE PRESENT INVENTION

The inventors have found that by varying the size of the holes incrementally along the legs of the U tube blanket, for example from the proximal portions of the legs that are closest to the air inlet cross section where heated air is input to the blanket to the distal portions of the legs that are furthest away from the cross section, the warm air vented from the differently dimensioned vent holes is more evenly distributed, thereby providing for an evenly distributed layer of warm air for the patient.

It is further found that if the vent holes along the length of each leg of the tube blanket were to be formed in at least two rows with the respective sizes of the holes incrementally varied along the length of the leg, so that when the blanket is inflated the rows of vent holes from the two legs of the blanket are in substantially opposed alignment with each other for directing the vented warm air to both sides of the patient positioned there between, the heated air output to the patient is more evenly distributed over the patient than prior tube blankets. Moreover, it was found that a more optimal and efficient warming U-tube blanket may be obtained if the vent holes along each leg of the blanket were to be grouped into sections along the length of the legs of the blanket, with the holes in each of the sections having the same dimension.

To secure the blanket to the patient, two straps are integrally formed from the inside rim or flange of each of the legs of the tube blanket, with one of the ends of each strap separable from the rim of the tube leg so that, when separated from the rim, the straps from the legs could be used as ties to secure the blanket to the patient.

It was found that it is necessary to have only one row of vent holes provided along each leg of the tube blanket for the inventive blanket to operate as desired. If per the illustrated embodiment, two rows of vent holes are provided along each leg of the blanket it was moreover found that the rows of vent holes along each leg of the U tube blanket should be formed along the respective legs such that the holes from each leg would face each other along the length of the opposing legs at the respective inner side of the tube, i.e, at the respective sides of the legs that sandwich the patient, when the blanket is inflated, so that the air output from those opposing holes are directed substantially to the sides of the patient.

The present invention therefore relates to an inflatable tube blanket comprising two legs connected by an air input cross section where a hose inlet is adaptable to be connected with an air hose of a convective warmer, the two legs being positioned to sandwich a patient placed therebetween. There is also an air input to the air inlet at the cross section to inflate the two legs, and holes provided along each of the legs through which air input to the blanket is vented, wherein the size of the holes at each of the legs incrementally increases toward the end of the leg away from said cross section.

The present invention also relates to a U-shaped tube blanket that comprises an air input cross section for receiving heated air from a convective warmer; two legs each extending from a corresponding end of the cross section, wherein said each leg includes holes extending substantially along the length thereof wherethrough the heated air vents, the holes having sizes that incrementally increase from a proximal portion adjacent the cross section to a distal section away from the cross section so that the amount of heated air output from the distal portion is greater than the amount of heated air output from the proximal portion of the legs to thereby provide substantially evenly distributed warmth from the heated air for a patient placed between the two legs.

The present invention further relates to a method of providing substantially evenly distributed warmth to a patient with warm air directed to his sides, comprising the steps of: (1) forming a U-tube blanket by bonding a top air impermeable layer to a bottom air impermeable layer at their respective edges so as to form at least one rim along the edges of the blanket, providing an air inlet cross section whereinto heated air from a convective warmer is input, and extending a leg from each end of the cross section; (2) forming holes of different sizes substantially along the length of each of the legs, with the size of the holes increasing from a proximal portion of each leg closest to the cross section to a distal portion of each leg away from the cross section; (3) placing the U-tube blanket about the patient; and (4) inputting heated air to the air inlet so that warm air is output from the holes along the tube legs with a higher volume of warm air outputting from the distal portion than the proximal portion of each of the legs to the patient.

BRIEF DESCRIPTION OF THE FIGURES

The present invention will become apparent and the invention will best be understood by reference to the following description taken in conjunction with the accompanying drawings, wherein.

DETAILED DESCRIPTION OF THE INVENTION

Figure 1:
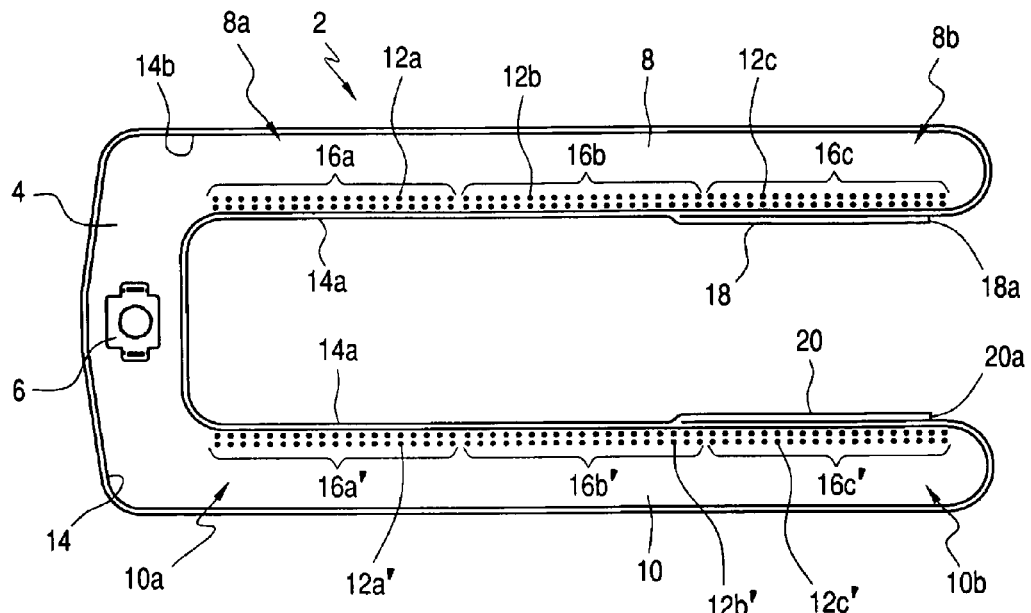
FIG. 1 is a top view of the U tube blanket of the instant invention.

With reference to FIG. 1, a U tube blanket 2 is shown to have an air inlet cross section 4 having an inlet orifice 6 into which heated air from a convective warmer (not shown) is input by means of a hose, as is commonly known. The input orifice 6 for the U tube blanket 2 may be configured with the type of input that is described in co-pending application Ser. No. 11/401,957, assigned to the same assignee as the instant invention. The disclosure of the '957 application is incorporated herein by reference.

Extending from each end of the cross section 4 is a leg 8, 10. Each of legs 8 and 10 in actuality is a continuation of the cross section 4, as the blanket is made from two layers of air impermeable materials that are bonded at their respective edges so that a continuous rim or flange 14 is formed around the blanket. When thus bonded, the blanket is inflatable when filled with fluid, which for a convective blanket is most likely heated air. In the case where one or more air inlets are formed at the edge of the blanket where the layers of air impermeable materials are bonded, there is no longer a continuous rim formed around the blanket. In that case, it is more correct to say that there is at least one rim formed at the edge of the blanket. For the discussion of the instant invention, the rims between legs 8 and 10 are deemed the interior rims 14a, whereas the outside flange or rims of the blanket are designated 14b.

A plurality of holes or air vents 16 are formed or provided along substantially the length of each of legs 8 and 10. For the illustrated embodiment, at least two rows of holes are provided along each leg. The holes are of different dimensions or sizes, with the size of the holes increasing incrementally from the proximal portion 8a closest to cross section 4 to the distal portion 8b furthest removed from cross section 4 of the tube blanket 2. Thus, holes 12b, 12b' would have a size that is greater than holes 12a, 12a'; and holes 12c, 12c' would have a size that is greater than holes 12b, 12b'. For the embodiment shown in FIG. 1, representative dimensions for vent holes 12a, 12a', 12b, 12b' and 12c, 12c' may have diameters of 0.050 inch, 0.150 inch and 0.250 inch, respectively. Although illustrated as having only three sizes, it should be appreciated that a plurality of other vent holes having different dimensions may also be utilized in the U tube blanket of the instant invention. Also it should be noted that although two rows of holes are shown along each leg of the illustrated embodiment blanket, in practice only one row of incrementally dimensioned holes, divided by sections or vary with no distinguishing sections along the length of the leg of the blanket, may also be used.

For the FIG. 1 embodiment, as noted above, the vent holes 12 are shown to be grouped into three exemplar sections 16a, 16b and 16c, although fewer or additional sections may also be used. Moreover, instead of sections, the successive vent holes may be configured to have increasing dimension from proximal portions 8a, 10a to distal portions 8b, 10b for legs 8 and 10, respectively, of the embodiment blanket, so that successively differently sized vent holes are formed along each of the legs of the blanket.

Each of exemplar sections 16a to 16c is shown to have two rows of 19 vent holes each. It should be appreciated that the number of vent holes provided for each section, as well as provided along the length of each leg of the blanket, is for illustration only and not limiting. The number of vent holes provided at each of sections 16 may for example range from 2 to more than 45, preferably between 15 and 25.

It has been found that the vent holes may have effective sizes ranging in diameter from approximately 0.025 inch to approximately 0.50 inch. For the embodiment blanket of FIG. 1, the vent holes at section 16a are formed with a dimension of approximately 0.050 inch, the vent holes at the middle section 16b are formed with an opening of approximately 0.150 inch, and the vent holes at section 16c are formed with a dimension of approximately 0.250 inch. By empirical study, the dimension of the size or diameter of the vent holes for the embodiment blanket was found to be most efficient at approximately 0.050 inch to 0.250 inch.

With the holes along each of legs 8, 10 being incrementally increased in sections so that the amount of heated air that is vented from the different sections would vary, the amount of warm air output from section 16c, 16c' is greater than that output from section 16a, 16a'. As a result, an evenly distributed warmth layer, resulting from the disparate amount of warm air output from the different sections, is provided to envelop the patient, for example patient 22 shown in FIGS. 2 and 3 who is placed between legs 8 and 10 of the blanket.

Figure 3:
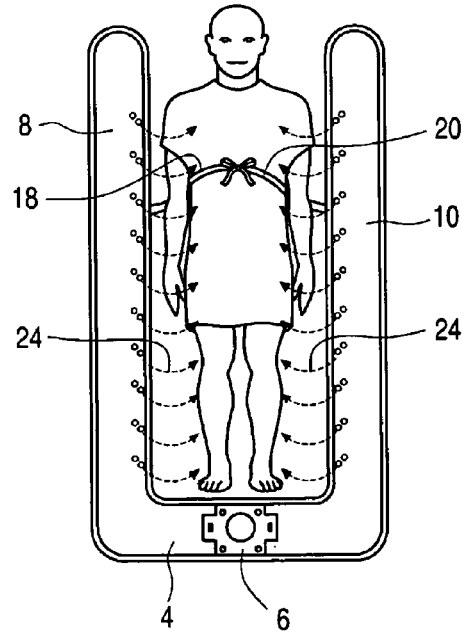
FIG. 3 shows the U tube blanket being tied to the patient and the air flow output from the legs of the blanket being directed to the patient.

With the U tube blanket inflated, as for example shown in FIG. 3, the rows of vent holes along the interior side of each of legs 8 and 10 would be in opposed alignment relationship with each other so that air output from those vent holes 12a-12c, 12a'-12c' are directed to both sides of the patient, as represented for example by the directional arrows 24.

Figure 2:
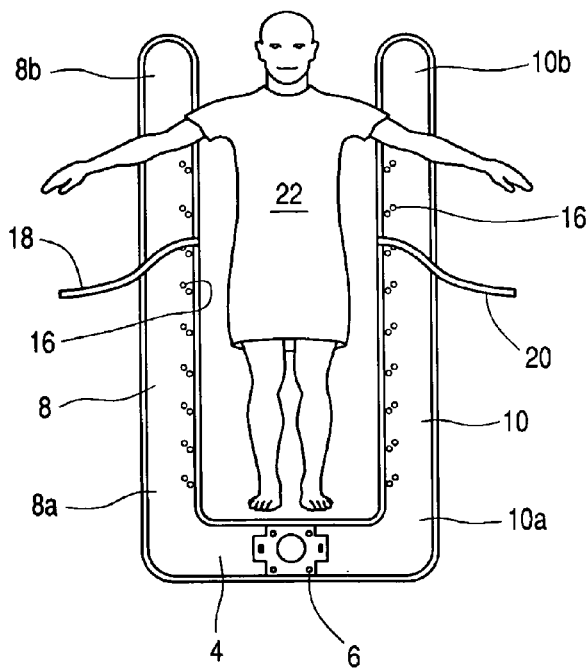
FIG. 2 is an illustration of the inventive U tube blanket placed relative to the patient, with the patient being sandwiched by the legs of the U tube blanket.

Also shown in FIGS. 1 and 2 are straps 18 and 20 integrally formed from interior rim or flange 14a of each of legs 8 and 10, with respective weakened ends 18a and 20a thereof that allow the straps 18 and 20 to be separable from the legs 8 and 10, and more specifically the interior rims 14a of the blanket. Each of straps 18 and 20 is configured from inner rim 14a in such a way that only one end 18a, 20a thereof is separable from inner rim 14a. As shown in FIG. 2, the straps, having their ends 18a and 20a separated from rim 14a, are freely lying next to patient 22. FIG. 3 shows straps 18 and 20 having been tied to secure the U tube blanket 2 to patient 22. The straps 18 and 20 may well be formed from the outer rims 14b.

With specific reference to the embodiment of FIGS. 2 and 3, U tube blanket 2 is shown to be positioned relative to patient 22 such that patient 22 is sandwiched by legs 8 and 10 of the blanket, with the feet of the patient being adjacent to the air inlet cross section 4 of the blanket. With the blanket thus positioned relative to the patient, the patient is heated or bathed by an evenly distributed envelope of warm air. Although FIGS. 2 and 3 show the feet of the patient being adjacent to cross section 4 and the head of the patient being at the open end of the U tube blanket 2, in practice the patient may be positioned relative to blanket 2 such that his head is adjacent to cross section 4 while his feet are at the open end of the blanket.

It should be appreciated that the present invention is subject to many variations, modifications and changes in detail. Accordingly, it is intended that the invention be limited only by the spirit and scope of the hereto appended claims.

The invention claimed is:

1. An inflatable tube blanket comprising: two legs each extending from an air input cross section where a hose inlet is adaptable to be connected with an air hose of a convective warmer, the two legs being positioned to sandwich a patient placed therebetween, air input to the air inlet at said cross section to inflate the two legs, a plurality of sections each having multiple holes provided along each of the legs through which air input to said blanket is vented, wherein the size of the holes at each of said plurality of sections being the same, the size of the holes in the section furthest away from said air input cross section being larger than the size of the holes in the section closest to said air input cross section, at least a third section separating the section furthest away from said air input cross section and the section closest to said air input cross section, the size of holes in the third section being smaller than the size of the holes in the section furthest away from said air input cross section but larger than the size of holes in the section closest to said air input cross section, respective straps each bonded to a rim at each of the legs that faces the patient, one end of each strap removable from the rim, the straps from each of the legs used to secure the blanket to the patient.

2. Blanket of claim 1, wherein there are at least two rows of holes extending substantially along the length of each of the legs.

3. Blanket of claim 1, wherein the holes at each of the legs are positioned to be in opposing alignment relationship to the holes at other of the legs when the blanket is inflated so that when the patient is placed between the two legs, air venting from the holes are directed to the patient.

4. Blanket of claim 1, wherein the holes have dimensions that range in diameter from approximately 0.025 to 0.50 inch and preferably from 0.050 to 0.250 inch.

5. Blanket of claim 1, wherein the holes along each of the legs are divided into three sections, with the holes at the section closest to the cross section each having a dimension of approximately 0.050 inch, the holes at the section furthest from the cross section each having a dimension of approximately 0.250 inch, and the holes at the section between the sections closest to and furthest from the cross section each having a dimension of approximately 0.150 inch, each of the sections has from approximately 2 to 40 holes and preferably from 15 to 25 holes.

6. A method of providing substantially evenly distributed warmth to a patient with warm air directed to his sides, comprising the steps of:
   forming a U-tube blanket by
       bonding a top air impermeable layer to a bottom air impermeable layer at their respective edges so as to form at least one rim along the edges of the blanket,
       providing an air inlet cross section whereinto heated air from a convective warmer is input,
       extending a leg from each end of the cross section,
       forming three sections of holes along the length of each of the legs, the sections including a proximal section that is closest to the cross section, a distal section that is furthest away from the cross section and a mid section that is between the proximal and distal sections, the size of the holes in each of the sections being the same within said each section but different from the other sections;
   forming the holes at the proximal section to have a dimension of approximately 0.050 inch, the holes at distal section to have a dimension of approximately 0.250 inch, and the holes at a middle section between the proximal and distal sections to have a dimension of approximately 0.150 inch; placing the U-tube blanket about the patient;
   securing the blanket to the patient; and
   inputting heated air to the air inlet so that warm air is output from the holes along the legs with a higher volume of warm air outputting from the distal portion than the proximal portion of each of the legs.

7. A U-shaped tube blanket, comprising:
   an air input cross section for receiving heated air from a convective warmer;
   two legs each extending from a corresponding end of said cross section for sandwiching a patient therebetween, wherein said each leg comprises a plurality of successive sections of holes extending substantially along the length of each leg, heated air venting from the holes, said sections extending along each leg from a proximal section of holes adjacent to said cross section to a distal section of holes away from said cross section, each of the sections having multiple holes of a given dimension, the size of the holes in each section being the same within said each section but different from the other sections, at least one mid section of holes of the same dimension between the proximal and distal sections, the dimension of the holes of the mid section being smaller than the holes of the distal section but larger than the holes of the proximal section, wherein the holes in each of the successive sections along each leg of the blanket have a dimension greater than the previous section so that the amount of heated air output from the distal portion is greater than the amount of heated air output from the proximal portion of the legs to thereby provide substantially evenly distributed warmth from the heated air for a patient placed between the two legs.

8. Blanket of claim 7, wherein there are three sections extending on each leg of the blanket, with the holes at the proximal section adjacent to the cross section each having a dimension of approximately 0.050 inch, the holes at the distal section furthest from the cross section each having a dimension of approximately 0.250 inch, and the holes at the mid section between the proximal and distal sections each having a dimension of approximately 0.150 inch.

9. Blanket of claim 7, wherein there are at least two rows of holes extending substantially along the length of each of the legs through the different sections, and wherein the holes at each of the legs are positioned to be in opposing alignment relationship to the holes at the other of the legs when the blanket is inflated so that when the patient is placed between the two legs, air venting from the holes are directed to the patient.

10. Blanket of claim 7, wherein each of the legs comprises a strap having one end removable from the leg so that both straps for the legs are adaptable to be used to secure the blanket to the patient.

\* \* \* \* \*